(12) United States Patent
Matsumoto

(10) Patent No.: US 9,980,680 B2
(45) Date of Patent: May 29, 2018

(54) RESPIRATORY DETECTION DEVICE

(71) Applicant: DENSO CORPORATION, Kariya, Aichi-pref. (JP)

(72) Inventor: Arihiro Matsumoto, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days. days.

(21) Appl. No.: 15/396,872

(22) Filed: Jan. 3, 2017

(65) Prior Publication Data

US 2017/0196516 A1    Jul. 13, 2017

(30) Foreign Application Priority Data

Jan. 13, 2016 (JP) ................. 2016-004125

(51) Int. Cl.
*B60R 22/00* (2006.01)
*A61B 5/00* (2006.01)
*A61B 5/08* (2006.01)
*A61B 5/113* (2006.01)
*A61B 5/18* (2006.01)
*B60K 28/06* (2006.01)

(52) U.S. Cl.
CPC .............. *A61B 5/6893* (2013.01); *A61B 5/08* (2013.01); *A61B 5/113* (2013.01); *A61B 5/18* (2013.01); *B60R 22/00* (2013.01); *A61B 2562/0261* (2013.01); *B60K 28/06* (2013.01); *B60Y 2400/30* (2013.01)

(58) Field of Classification Search
CPC ......... A61B 5/6893; A61B 5/113; A61B 5/08; A61B 5/18; A61B 2562/0261; B60R 22/00; B60L 28/06; B60Y 2400/30
See application file for complete search history.

(56) References Cited

U.S. PATENT DOCUMENTS

| 5,990,795 A * | 11/1999 | Miller .................... G08B 21/06 180/272 |
| 6,195,008 B1 * | 2/2001 | Bader ............... B60R 21/01516 180/271 |
| 7,576,642 B2 * | 8/2009 | Rodemer ........... A61B 5/02438 280/735 |
| 2006/0155175 A1 | 7/2006 | Ogino et al. |
| 2006/0290516 A1 * | 12/2006 | Muehlsteff ........... A61B 5/0265 340/573.1 |

(Continued)

FOREIGN PATENT DOCUMENTS

JP        H02-246837 A    10/1990
JP        2005-095408 A    4/2005

*Primary Examiner* — Drew J Brown
(74) *Attorney, Agent, or Firm* — Harness, Dickey & Pierce, P.L.C.

(57) ABSTRACT

A respiratory detection device detects a behavior of breathing of an occupant on a seat of a vehicle. A seatbelt is equipped by the occupant to retain the occupant at the seat. A detection belt is mounted to the vehicle or the seat at one-end side. The detection belt is further connected to the seatbelt at the other-end side. The detection belt is equipped by the occupant together with the seatbelt when the occupant equips the seatbelt. A sensor is connected to the detection belt to detect the behavior of breathing. The detection belt retains the sensor at a position of an abdomen of the occupant when the occupant equips the seatbelt.

4 Claims, 6 Drawing Sheets

(56) References Cited

U.S. PATENT DOCUMENTS

| | | | |
|---|---|---|---|
| 2010/0222687 A1* | 9/2010 | Thijs | A61B 5/02438 600/508 |
| 2012/0078122 A1* | 3/2012 | Yokoyama | A61B 5/0245 600/484 |
| 2013/0033382 A1* | 2/2013 | Fung | A61B 5/6893 340/573.1 |
| 2015/0265200 A1* | 9/2015 | Mahdi | A61B 5/0205 600/301 |
| 2017/0296128 A1* | 10/2017 | Aoki | A61B 5/024 |
| 2018/0020984 A1* | 1/2018 | Hall | A61B 5/6891 |

* cited by examiner

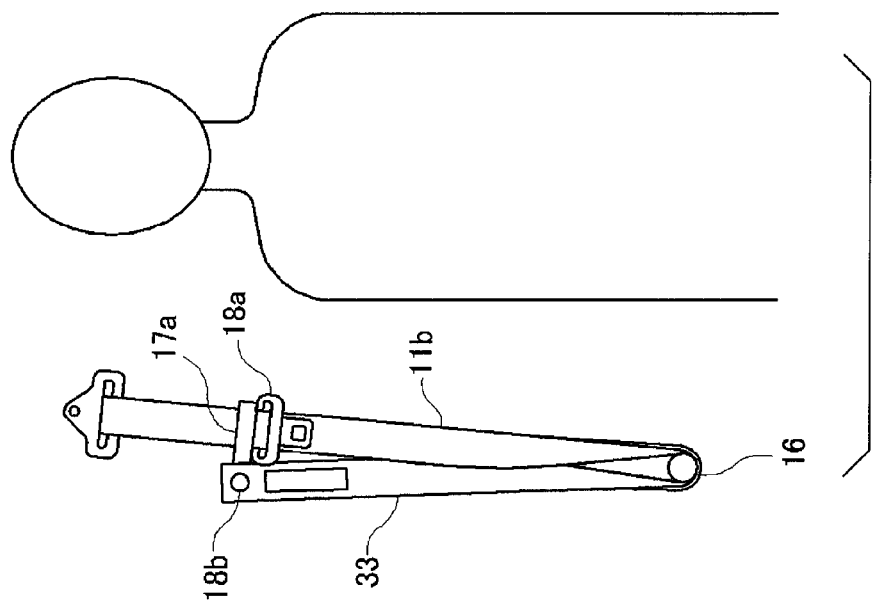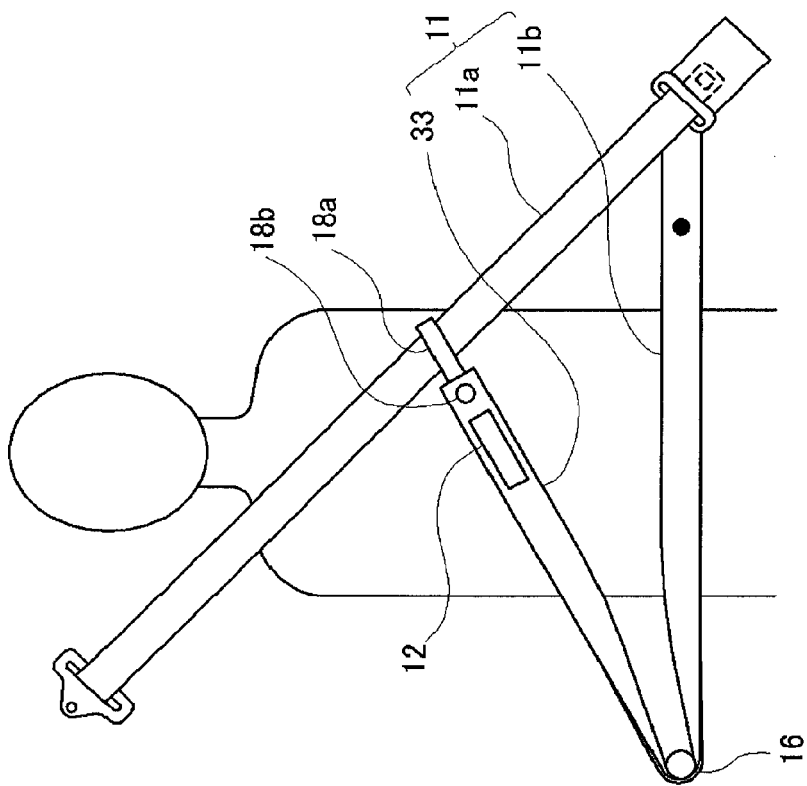

RESPIRATORY DETECTION DEVICE

CROSS REFERENCE TO RELATED APPLICATION

This application is based on Japanese Patent Application No. 2016-4125 filed on Jan. 13, 2016, the disclosure of which is incorporated herein by reference.

TECHNICAL FIELD

The present disclosure relates to a respiratory detection device configured to detect a state of breathing of an occupant by utilizing a sensor equipped to a seatbelt of a vehicle.

BACKGROUND

In recent years, technology for detecting a state of breathing of an occupant has been developed. Grasping of the state of breathing of an occupant can be applied to various technological fields. For example, in a condition where an occupant is hard to continue a driving operation due to, for example, sudden illness, it is conceivable that a length, a depth, and/or the like of breathing differ from those of breathing in a normal state. In consideration of this, a configuration, which enables detection of the state of breathing of an occupant with sufficient accuracy, would be able to avoid a traffic accident. For example, in a case where an occupant gets difficult to continue a driving operation of a vehicle and on detection of the occupant's state, the driving operation of the occupant may be switched to an automatic control to cause a vehicle to stop its traveling.

For example, Patent Literature 1 proposes a technology to equip a sensor in a belt portion of a seatbelt for detecting a state of breathing of an occupant. In the configuration where the sensor is equipped to the seatbelt, an occupant would be equipped with the sensor simultaneously when the occupant equips the seatbelt. In a configuration where the sensor equipped to the seatbelt is capable of detecting a state of breathing of an occupant, the configuration does not require the occupant an additional and exclusive operation to equip the sensor.

Patent Literature 1

Japanese Unexamined Patent Publication No. H2-246837

It is noted that, the configuration proposed by Patent Literature 1, in which the sensor is equipped to the seatbelt to detect a state of breathing of an occupant, may not be able to detect the state of breathing with sufficient accuracy.

SUMMARY

It is an object of the present disclosure to produce a respiratory detection device configured to detect a state of breathing of an occupant with sufficient accuracy without requiring an occupant a burden to equip a sensor.

As described above, the configuration proposed by Patent Literature 1, in which a sensor is equipped to a seatbelt to detect a state of breathing of an occupant, may not be able to detect the state of breathing with sufficient accuracy. The reason is as follows.

To begin with, a seatbelt is designed to support an occupant at a skeleton portion of the occupant in order to enable to retain the occupant on a seat even when an accident occurs. For example, a three-point seatbelt is generally equipped to a driver's seat. A general three-point seatbelt includes a shoulder belt and a waist belt. The shoulder belt is a belt portion extending aslant from an occupant's shoulder to an occupant's waist. The waist belt is a belt portion equipped to the occupant's waist. The seatbelt retains an occupant at the skeleton portion in this way. Therefore, when an occupant's body moves with a driving operation, such as a steering handle operation, an accelerator operation, and/or a brake operation, its influence appears significantly in the seatbelt. Because of this reason, the configuration, in which a sensor is equipped simply to a seatbelt, would produce an output signal, which is intensely affected by a driving operation rather than occupant's breathing. Therefore, this configuration would hardly detect a state of breathing of an occupant with sufficient accuracy.

According to an aspect of the present disclosure, a respiratory detection device is configured to detect a behavior of breathing of an occupant on a seat of a vehicle. The respiratory detection device comprises a seatbelt configured to be equipped by the occupant to retain the occupant at the seat. The respiratory detection device further comprises a detection belt mounted to the vehicle or the seat at one-end side. The detection belt is connected to the seatbelt at an other-end side. The detection belt is configured to be equipped by the occupant together with the seatbelt when the occupant equips the seatbelt. The respiratory detection device further comprises a sensor connected to the detection belt and configured to detect the behavior of breathing. The detection belt is configured to retain the sensor at a position of an abdomen of the occupant when the occupant equips the seatbelt.

BRIEF DESCRIPTION OF THE DRAWINGS

The above and other objects, features and advantages of the present invention will become more apparent from the following detailed description made with reference to the accompanying drawings. In the drawings:

FIG. 5A is a view showing a respiratory detection device according to a modification in the equipped state, the respiratory detection device including an extension belt formed by extending the seatbelt to be a component equivalent to the sensor belt, and FIG. 5B is a view showing the respiratory detection device in the stored state.

DETAILED DESCRIPTION

Embodiment

In the following description, embodiments of the present disclosure will be described.

(Configuration of Device According to Present Embodiment)

Figure 1:
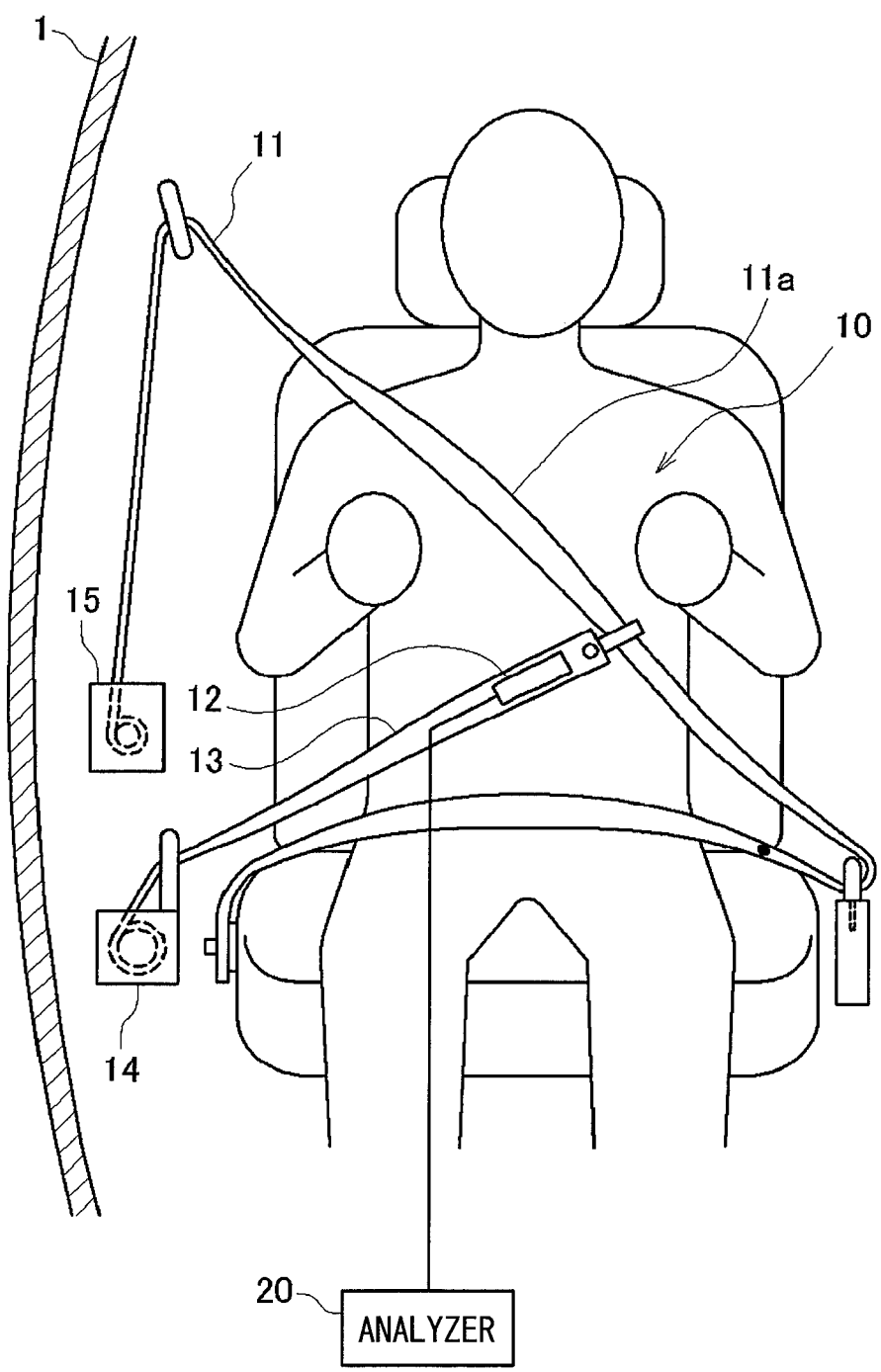
FIG. 1 is a view showing a state where an occupant is equipped with a respiratory detection device according to an embodiment.

FIG. 1 shows an interior of a vehicle 1 equipped with a respiratory detection device 10 according to the present embodiment. As shown in the drawing, the respiratory detection device 10 includes a seatbelt 11, a sensor 12, a sensor belt (detection belt) 13, and a winding device 14. The seatbelt 11 is equipped to the vehicle 1. The sensor 12 is for detecting behavior of driver's breathing. The sensor belt 13 is configured to be equipped with the sensor 12. The winding device 14 is for applying a tensional force onto the sensor belt 13. The seatbelt 11 is a three-point seatbelt equipped by an occupant such that a singular belt is supported at three points. The seatbelt 11 is wound up by a winding device 15 when being stored. To the contrary, as shown in the drawing, when the seatbelt 11 is equipped by an occupant, a shoulder belt 11a is formed to press a region from a shoulder of an occupant such as a driver to a chest of the occupant.

The sensor 12 is mounted to the sensor belt 13. The sensor 12 is configured to measure a physical quantity such as a tensional force, which is applied to the sensor belt 13, and a flexure of the sensor belt 13. The sensor 12 may employ various configurations such as a strain gauge type configuration and/or a piezo type configuration. The sensor belt 13 is configured such that the sensor belt 13 is connected to the shoulder belt 11a at one end (one-end side), and the sensor 12 is located at an abdomen of an occupant in a state where the occupant is equipped with the seatbelt 11. The sensor belt 13 has the other end (other end side) on the opposite side of the shoulder belt 11a, and the other end of the sensor belt 13 is connected to the winding device 14. The winding device 14 is located at a specific position, which is between a position lateral to an occupant and a position on a rear side of the occupant in a front-rear direction, The specific position of the winding device 14 is on a lower side of the occupant in a vertical direction. The winding device 14 is configured to apply a tensional force onto the sensor belt 13. In this manner, the sensor belt 13 is maintained to be in contact with an occupant. Therefore, the sensor 12 is enabled to measure, via the sensor belt 13, a motion of an abdomen caused by breathing of an occupant.

An analyzing device 20 is connected to the sensor 12. The analyzing device 20 is configured to analyze a measurement result of the sensor 12 to enable to detect a state of breathing of an occupant. The analyzing of the measurement result may employ various analysis methods, and therefore, description of details of the analyzing procedure is omitted. Generally, an abdomen of an occupant repeats swelling and denting. In consideration of this, the state of breathing of an occupant is detectable according to a measured motion of the abdomen. As described above, the respiratory detection device 10 according to the present embodiment includes the sensor 12 for detecting the state of breathing. According to the present configuration, the sensor 12 is equipped to the sensor belt 13 such that the sensor 12 is located at an occupant's abdomen. Therefore, the present configuration enables to enhance a detection accuracy of breathing. The reason will be described as follows.

To begin with, a sensor of a conventional respiratory detection device for detecting a state of breathing has been equipped to a seatbelt. It is noted that, a seatbelt is designed to press a skeleton portion of an occupant. Therefore, when an occupant turns a vehicle wheel and/or when an occupant depresses a brake pedal, a body of an occupant also moves. Therefore, the seatbelt, which presses the occupant at the skeleton portion, also moves along with a driving operation of the occupant. Consequently, a measurement result of the sensor excessively reflects a movement of a driving operation, in addition to reflecting a movement of breathing. Therefore, a conventional sensor would be hardly configured to detect a state of breathing correctly. To the contrary, the respiratory detection device 10 according to the present embodiment includes the sensor 12 separately (exclusively) from the seatbelt 11, such that the sensor 12 is located at an abdomen of an occupant. Generally, a skeleton is away from a surface of an abdomen in a human body. Therefore, in general, an abdomen does not have a skeleton and is soft. Even when an occupant's body moves along with a driving operation, the movement of the occupant's body may be absorbed by an abdomen of the occupant. Thus, the movement of the occupant's body is hardly transmitted to the sensor 12 located at the abdomen. Consequently, a driving operation exerts small influence on the detection result of breathing. In addition, a motion caused by breathing is generally greater at an abdomen than a motion at a shoulder and/or a chest. Therefore, the configuration where the sensor 12 is mounted on the abdomen facilitates detection of the state of breathing. Also because of this reason, the respiratory detection device 10 according to the present embodiment is configured to detect the state of breathing sufficiently with higher accuracy than a conventional respiratory detection device.

With the present configuration, the respiratory detection device 10 according to the present embodiment is configured to detect the state of breathing of an occupant with sufficient accuracy. Therefore, the respiratory detection device 10 may be applicable to various technological purposes. For example, in a case where the respiratory detection device 10 becomes unable to detect breathing of an occupant during the vehicle 1 travels, it may be conceivable that the occupant would be unable to continue the driving operation due to, for example, sudden death or a cardiopulmonary arrest. In such a case, the driving operation may be switched to an automatic-controlled operation to cause a vehicle-side device, such as a dead-man device, to terminate the travelling of the vehicle. It is noted that, even if an occupant is unable to implement a driving operation, the occupant does not necessarily terminate breathing. Nevertheless, it is further noted that, in a case where the occupant is in such a critical condition where the occupant cannot continue the driving operation, it is conceivable that occupant's breathing in this state is different from occupant's breathing in a normal state. For example, in a case where an occupant causes heart failure and/or cerebral hemorrhage, Cheyne-Stokes respiration may be observed. Cheyne-Stokes respiration has a characteristic breathing pattern in which a length and a depth of breathing vary periodically. The respiratory detection device 10 according to the present embodiment is capable of reducing an influence, which is caused by a driving operation, and therefore is capable of detecting a state of breathing. Therefore, the respiratory detection device 10 has a configuration in which termination hardly arises in detection of breathing during a driving operation. Thus, the respiratory detection device 10 is configured to grasp a length of breathing correctly. In addition, the respiratory detection device 10 has a configuration in which small influence would arise due to a driving operation, thereby to enable to sufficiently reflect a motion of an abdomen, which is caused by breathing, on the detection result of the sensor 12. Therefore, the respiratory detection device 10 is configured to grasp a depth of breathing correctly. Thus, the respiratory detection device 10 is enabled to detect a characteristic breathing pattern correctly according to a length and/or a depth of breathing.

Application of the respiratory detection device 10 according to the present embodiment is not limited to the above-described dead man device. The respiratory detection device 10 may be applied to other various technological purposes. For example, when an occupant is in an asleep state, occupant's breathing becomes calmer than breathing in an awakening state. Therefore, the respiratory detection device 10 is enabled to detect that the occupant fell asleep according to the length and the depth of breathing. Alternatively of in addition, the respiratory detection device 10 is enabled to estimate that an occupant becomes irritated and is in an excited state according to a state where breathing becomes short and shallow. A length and a depth of breathing have an individual difference. In consideration of this, the respiratory detection device 10 may store a respiratory state of an occupant in a normal state and may compare the stored respiratory state with a present respiratory state. In this way, the respiratory detection device 10 may enhance an accuracy of determination of the asleep state and/or the excited state.

As described above, the respiratory detection device 10 according to the present embodiment is applicable to various technological purposes due to, for example, equipment of the sensor 12 at an abdomen of an occupant thereby to enable the sensor 12 to detect a state of breathing with a high accuracy. Furthermore, the respiratory detection device 10 according to the present embodiment is configured to locate the sensor 12 at an abdomen of an occupant, without imposing an additional burden on an occupant. As follows, details for the configuration will be described.

Figure 2:
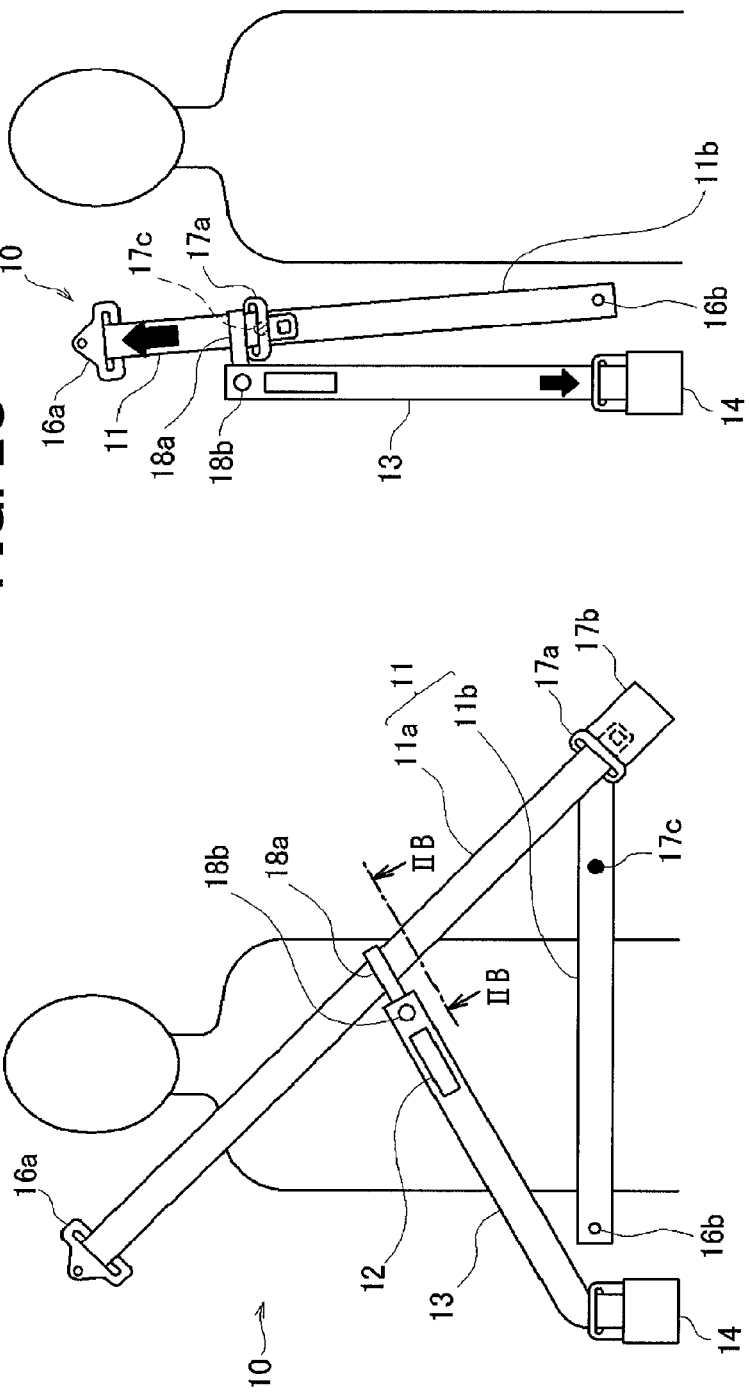
FIG. 2A is a view showing the respiratory detection device in an equipped state.
FIG. 2B is a sectional view taken along a line IIB-IIB in FIG. 2A.
FIG. 2C is a view showing the respiratory detection device in a stored state.

FIGS. 2A and 2B show an equipped state and a stored state of the respiratory detection device 10, respectively. First, the equipped state in FIG. 2A will be described. The seatbelt 11 of the respiratory detection device 10 may be a generally-known seatbelt. As shown in the drawing, the seatbelt 11 is supported at three points including an upper guide 16a, a lower fixture 16b, and an attachment-and-detachment plate 17a. The upper guide 16a is equipped on an upper side in an occupant's seat (driver's seat). The lower fixture 16b is equipped on a lower side in the occupant's seat. The attachment-and-detachment plate 17a is affixed when the occupant equips the seatbelt 11. The seatbelt 11 has a tip end, which is mounted with the lower fixture 16b at an attachment portion, such that the attachment portion is rotational. The seatbelt 11 has an opposite end opposite from the tip end. The opposite end of the seatbelt 11 is connected to the winding device 15 (refer to FIG. 1) at a rear side of the upper guide 16a.

The attachment-and-detachment plate 17a has an annular portion having a width larger than a width of the seatbelt 11. The seatbelt 11 is inserted through the annular portion of the attachment-and-detachment plate 17a, such that the seatbelt 11 is slidable and movable relative to the attachment-and-detachment plate 17a. A buckle 17b is equipped on an opposite side of the occupant's seat from the lower fixture 16b. An occupant inserts the attachment-and-detachment plate 17a into the buckle 17b thereby to be equipped with the seatbelt 11. In the present state, the seatbelt 11 has the shoulder belt 11a and a waist belt 11b. The shoulder belt 11a is located closer to the upper guide 16a than the attachment-and-detachment plate 17a. The waist belt 11b is located close to the lower fixture 16b than the attachment-and-detachment plate 17a. The stopper 17c is affixed to the waist belt 11b. The stopper 17c is a component, which may be generally equipped to a seatbelt. The stopper 17c is formed to have a size such that the stopper 17c is unable to pass through the annular portion of the attachment-and-detachment plate 17a. The stopper 17c having the present configuration restricts the attachment-and-detachment plate 17a from falling when the seatbelt 11 is stored. A stored state will be described later in detail.

The respiratory detection device 10 is equipped with the sensor 12 by utilizing the seatbelt 11, which may have a general configuration. Specifically, the sensor 12 is mounted to the sensor belt 13, the one end of the sensor belt 13 is connected to the winding device 14, and the other end of the sensor belt 13 is connected to the shoulder belt 11a of the seatbelt 11. The sensor belt 13 is connected with the shoulder belt 11a at a connecting portion. The connecting portion of the sensor belt 13 is equipped with a sliding ring 18a and a rotational axis 18b. The sliding ring 18a and the rotational axis 18b will be described as follows.

FIG. 2B is a sectional view taken along a line IIB-IIB in FIG. 2A. As shown in the drawings, the sliding ring 18a is an annular member formed of a material having a flexibility. The shoulder belt 11a is inserted in the sliding ring 18a, such that the sliding ring 18a is slidable and movable relative to the shoulder belt 11a. The sliding ring 18a has an interior in size such that the attachment-and-detachment plate 17a is unable to pass through the sliding ring 18a. The reason will be described later. The sliding ring 18a is attached to the tip end of the sensor belt 13 via the rotational axis 18b. The rotational axis 18b is equipped perpendicularly to a belt surface of the sensor belt 13. The present configuration enables a sliding ring 13a to rotate along the belt surface of the sensor belt 13 such that the sliding ring 13a swings like a neck. The sliding ring 18a and the rotational axis 18b enable the tip end of the sensor belt 13 to be slidable and movable relative to the shoulder belt 11a and to change a connection angle relative to the shoulder belt 11a.

Subsequently, the stored state of the respiratory detection device 10 will be described with reference to FIG. 2C. To begin with, in the equipped state shown in FIG. 2A, when the attachment-and-detachment plate 17a is detached from the buckle 17b, the seatbelt 11 begins to be wound up by the winding device 15 (refer to FIG. 1). As shown in FIG. 2C, when the winding up is completed, the seatbelt 11 is in the stored state, in which the seatbelt 11 is stretched in the vertical direction from the tip end affixed to the lower fixture 16b to a portion which passes through the upper guide 16a. The stopper 17c, which is affixed to the seatbelt 11, is formed to have the size such that the stopper 17c is incapable of passing through the annular portion of the attachment-and-detachment plate 17a. Therefore, in the present state, the attachment-and-detachment plate 17a is supported by the stopper 17c and is suspended at an upper portion of the seatbelt 11.

In this way, when the seatbelt 11 is stored, the sensor belt 13 is also stored in a state to be described subsequently. Thus, the respiratory detection device 10 as a whole is in the stored state. To begin with, as described above, the interior of the sliding ring 18a, which connects the sensor belt 13 with the seatbelt 11, is configured to restrict the attachment-and-detachment plate 17a from passing therethrough. In addition, the sliding ring 18a is located closer to the upper guide 16a than the attachment-and-detachment plate 17a (refer to FIG. 2A). With the present structure, in the state where the seatbelt 11 is in the stored state and where the attachment-and-detachment plate 17a is located at the upper portion of the seatbelt 11, the sliding ring 18a is supported by the stopper 17c via the attachment-and-detachment plate 17a. Thus, the sliding ring 18a is located at an upper portion of the seatbelt 11.

It is noted that, the winding device 14 is located on the opposite side of the sensor belt 13 from the sliding ring 18a.

The winding device 14 is located at the lower portion in the occupant's seat. With the present structure, the sensor belt 13 is in the stored state where the sensor belt 13 is stretched in the vertical direction from the tip end, which is equipped with the sliding ring 18*a,* to a portion, which is wound up by the winding device 14. In the present state, if a force, which is to wind up the sensor belt 13 is set to be greater than a force, which is to wind up the seatbelt 11, the sliding ring 18*a* may depress downward the attachment-and-detachment plate 17*a*. In consideration of this, the force, which is caused by the winding device 14 to wind up the sensor belt 13, is set to be less than the force, which is caused by the winding device 15 to wind up the seatbelt 11. In this manner, the position of the attachment-and-detachment plate 17*a* is maintained at the upper portion of the seatbelt 11, similarly to a usual (normal) seatbelt. In this way, the present configuration facilitates an occupant to hold the attachment-and-detachment plate 17*a* to be equipped with the seatbelt 11. It is noted that, FIG. 2C illustrates the seatbelt 11 and the sensor belt 13 to be stretched and extended at different positions, in order to facilitate understanding the configuration. It is noted that, installation portions of the lower fixture 16*b* and the winding device 14 may be adjusted to enable the seatbelt 11 and the sensor belt 13 to be overlapped and stored in a compact form.

As above, the operation of the respiratory detection device 10 according to the present embodiment has been described where an occupant releases the seatbelt 11 in the equipped state shown in FIG. 2A to render the seatbelt 11 in the stored state shown in FIG. 2C. Similarly, an occupant may simply be equipped with the seatbelt 11 in order to change the respiratory detection device 10 in the stored state into the equipped state. In this case, as described below in detail, the sensor 12 comes to be located at an abdomen of an occupant without requiring an additional operation to the occupant.

Figure 3:
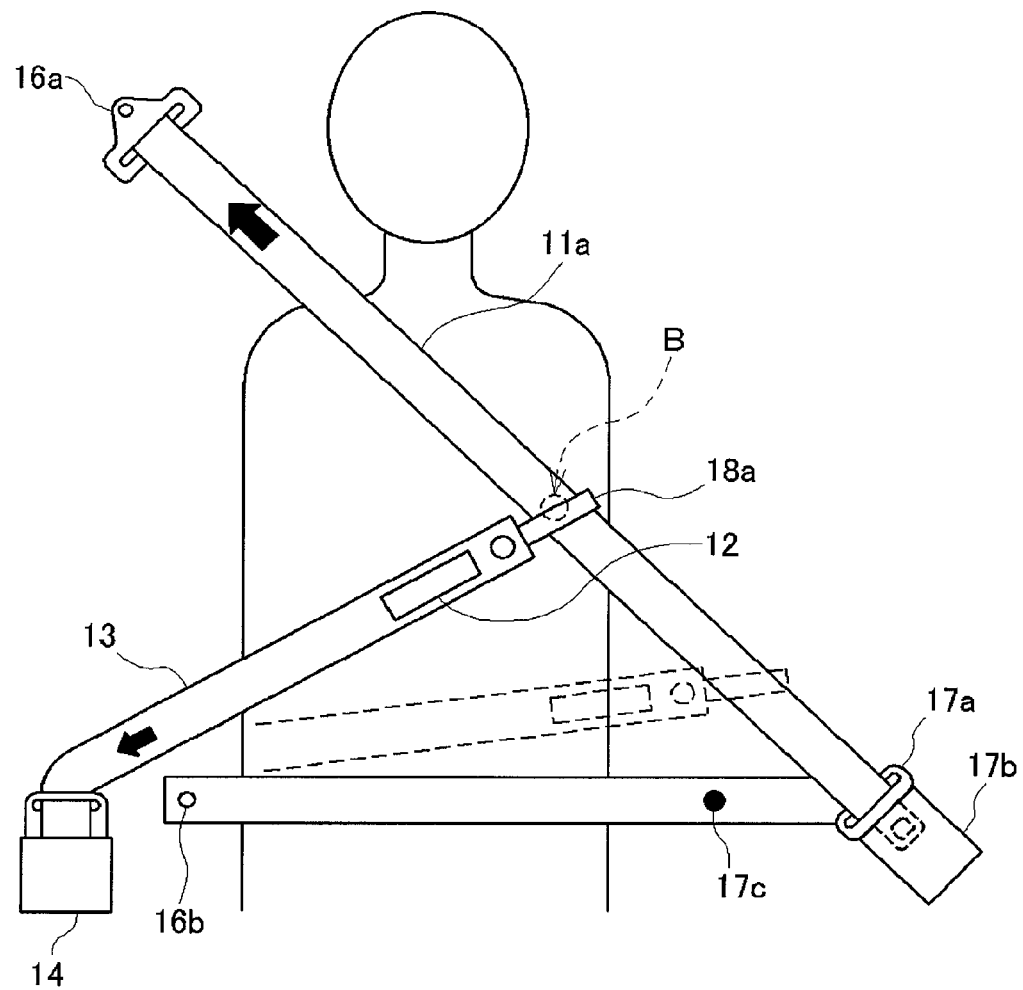
FIG. 3 is a view showing a position of a sensor of the respiratory detection device when an occupant is equips a seatbelt.

FIG. 3 shows a position of the sensor 12 at the time when an occupant is equipped with the seatbelt 11. As described above, the sensor belt 13 is connected to the shoulder belt 11*a* via the sliding ring 18*a*. In addition, the sensor belt 13 is slidable and movable relative to the shoulder belt 11*a*. Therefore, as shown by dashed lines in FIG. 3, when an occupant inserts the attachment-and-detachment plate 17*a* into the buckle 17*b* to be equipped with the seatbelt 11, the sensor belt 13 may be possibly located closer to the attachment-and-detachment plate 17*a*. It is noted that, the winding device 14 applies the force on the sensor belt 13 to wind up the sensor belt 13, and thereby the sensor belt 13 tends to be shortened. Therefore, the sensor belt 13 is applied with a force to be moved toward the upper guide 16*a*. Consequently, as shown in FIG. 3, the sensor belt 13 is moved in a state where the sensor 12 is located at an abdomen of an occupant. As described above, the present configuration may allow to set the installation positions of the occupant's seat, the seatbelt 11, and the winding device 14 at suitable positions and to adjust the winding-up force of the winding device 14 at a suitable force. By this setting and adjusting, the respiratory detection device 10 according to the present embodiment enables to locate the sensor 12 at an abdomen of an occupant when the occupant is equipped with the seatbelt 11.

In addition, the present configuration allows to affix the stopper to the shoulder belt 11*a*. The stopper has the size disabling the sliding ring 18*a* to pass therethrough, By this affixing of the stopper, an upper limit of the position, to which the sensor belt 13 is slidable relative to the shoulder belt 11*a,* can adjusted. For example, the stopper equipped at a position shown by B in FIG. 3 disables movement of the sensor belt 13 upward beyond the stopper. In the present state, the position of the sensor belt 13 is maintained at the position B equipped with the stopper. It is noted that, when the seatbelt 11 is stored, a portion of the seatbelt 11 at the position B passes through the upper guide 16*a*. In consideration of this, the annular portion of the upper guide 16*a,* through which the seatbelt 11 is passed through, is enlarged sufficiently to enable the stopper to pass therethrough.

Modification 1

As follows, modifications the respiratory detection device 10 according to the above-described embodiment will be described. Each modification includes a different configuration from that of the respiratory detection device 10. In the following description, the different configuration will be mainly explained.

In the above-described embodiment, the seatbelt 11 is inserted through the annular sliding ring 18*a,* which is connected to the sensor belt 13, in order to enable the sensor belt 13 to be slidable and movable relative to the seatbelt 11. It is noted that, the configuration, which is to enable the sensor belt 13 to be slidable and movable relative to the seatbelt 11, is not limited to this configuration. Other configuration may be employable to the configuration.

Figure 4A:
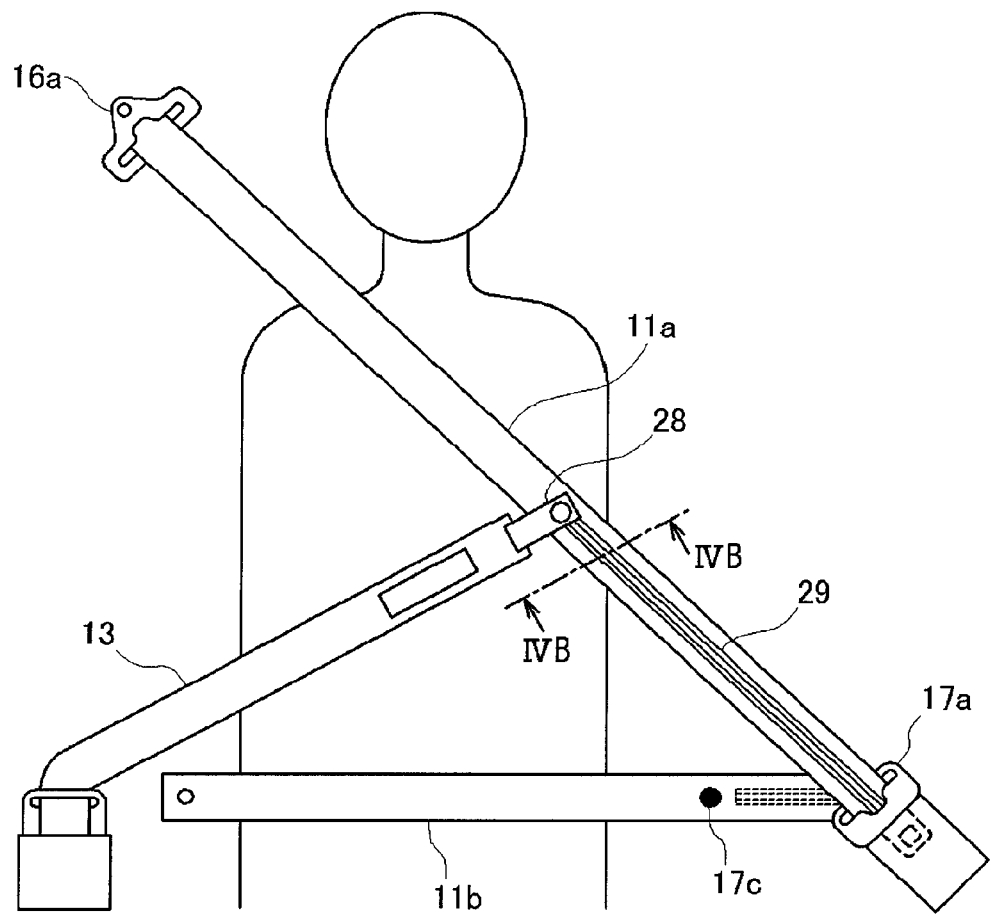
FIG. 4A is a view showing a modification of the respiratory detection device in which a rail enables a sensor belt to slide and to move relative to a seatbelt.

For example, as shown in FIG. 4A, rails 29 may be equipped to the seatbelt 11 to enable a connection member 28, which is equipped to the tip end of the sensor belt 13, to be slidable and movable. As follows, the connection member 28 and the rails 29 will be described.

Figure 4B:
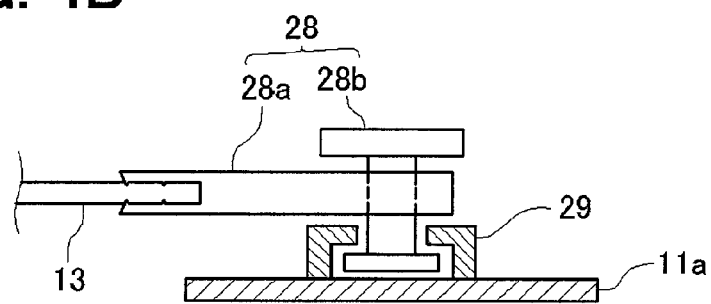
FIG. 4B is a sectional view taken along a line IVAB-IVB in FIG. 4A.

FIG. 4B is a sectional view taken along a line IVA-IVA in FIG. 4A. As shown in the drawing, the connection member 28 includes an affixed portion 28*a* and a slider 28*b*. The affixed portion 28*a* is affixed to the tip end of the sensor belt 13. The slider 28*b* is rotational relative to the affixed portion 28*a* and is slidable inside the rails 29 of the shoulder belt 11*a*. The rails 29 include a pair of a right rail and a left rail interposing the slider 28*b* from both sides. Tip ends of the right rail and a left rail are bent inward to restrict the slider 28*b* from falling off. The rails 29 are formed of a soft material so that the rails 29 are bendable integrally with the seatbelt 11. A length of the rails 29, which are formed in the seatbelt 11 along a longitudinal direction of the seatbelt 11, is set in a following manner.

First, as shown in FIG. 4A, upper ends of the rails 29 are set at predetermined positions in the shoulder belt 11*a*. In this way, the upper ends of the rails 29 are enabled to produce an effect to regulate the position of the sensor belt 13 in the equipped state, similarly to the equipment of the stopper at the position as previously described with reference to FIG. 3B. Referring to FIG. 2C, in the stored state, the tip end of the sensor belt 13 is located immediately above the stopper 17*c,* which is affixed to the seatbelt 11. In consideration of this, as shown in FIG. 4A, the rails 29 are extended such that the lower ends of the rails 29 are located at the position of the stopper 17*c* in the waist belt 11*b*. In the present configuration, the rails 29 pass through the attachment-and-detachment plate 17*a*. In consideration of this, the annular portion of the attachment-and-detachment plate 17*a* is formed to be in a shape to enable the rails 29 to pass through the annular portion. Similarly, the upper guide 16*a* is formed to be in a shape to enable the rails 29 to pass through the upper guide 16*a*.

The connection member 28 and the rails 29 are equipped in the above-described form. In this way, similarly to the above-described configuration equipped with the sliding ring 13a, the sensor belt 13 is enabled to be slidable and movable relative to the seatbelt 11. It is noted that, instead of the rails 29, a slit may be formed in the seatbelt 11. In this case, the connection member of the sensor belt 13 may be interposed in the slit of the seatbelt 11 to be slidable and movable relative to the slit of the seatbelt 11.

Modification 2

In the above-described embodiments, the sensor belt 13 is a separate and distinctive component from the seatbelt 11. The present disclosure is not limited to the above-described configurations. A member corresponding to the sensor belt 13 may be formed by extending the seatbelt 11. FIGS. 5A and 5B show the equipped state and the stored state of the respiratory detection device 10, respectively, having the configuration with an extension belt 33 formed by extending the seatbelt 11. As shown in FIG. 5A, the seatbelt 11 in the equipped state forms the extension belt 33 in addition to the shoulder belt 11a and the waist belt 11b, which are similar to those in the above-described embodiments. In the present modification, a turning device 16 is equipped instead of the lower fixture 16b, which is equipped in the above-described embodiments. The extended portion of the waist belt 11b of the seatbelt 11 is turned around the turning device 16 to be the extension belt 33. Similarly to the above-described embodiments, the sliding ring 18a and the rotational axis 18b enable a tip end of the extension belt 33 to be slidable and movable relative to the shoulder belt 11a and to modify an angle at the connection therebetween. The sensor 12 for detecting a state of breathing of an occupant is equipped similarly to the above-described embodiment.

The extension belt 33 is applied with a tensional force from the winding device 15 (refer to FIG. 1) for the seatbelt 11. Therefore, the extension belt 33 makes contact with an abdomen of an occupant. In this way, the sensor 12 equipped to the extension belt 33 is enabled to detect a state of breathing of an occupant. In this present modification, the winding device 14 employed in the above-described embodiments becomes unnecessary. In addition, as shown in FIG. 5B, when the attachment-and-detachment plate 17a is detached from the buckle 17b and when the seatbelt 11 is set in the stored state, the extension belt 33 is set in the stored state, similarly to the sensor belt 13 being stored (refer to FIG. 2C).

Modification 3

In above-described embodiments, a motion of an abdomen of an occupant is detected via the sensor belt 13. The configuration to detect a motion of an abdomen of an occupant is not limited to the above-described embodiments. A motion of an abdomen of an occupant may be detected between the sensor belt 13 and the seatbelt 11.

Figure 6:
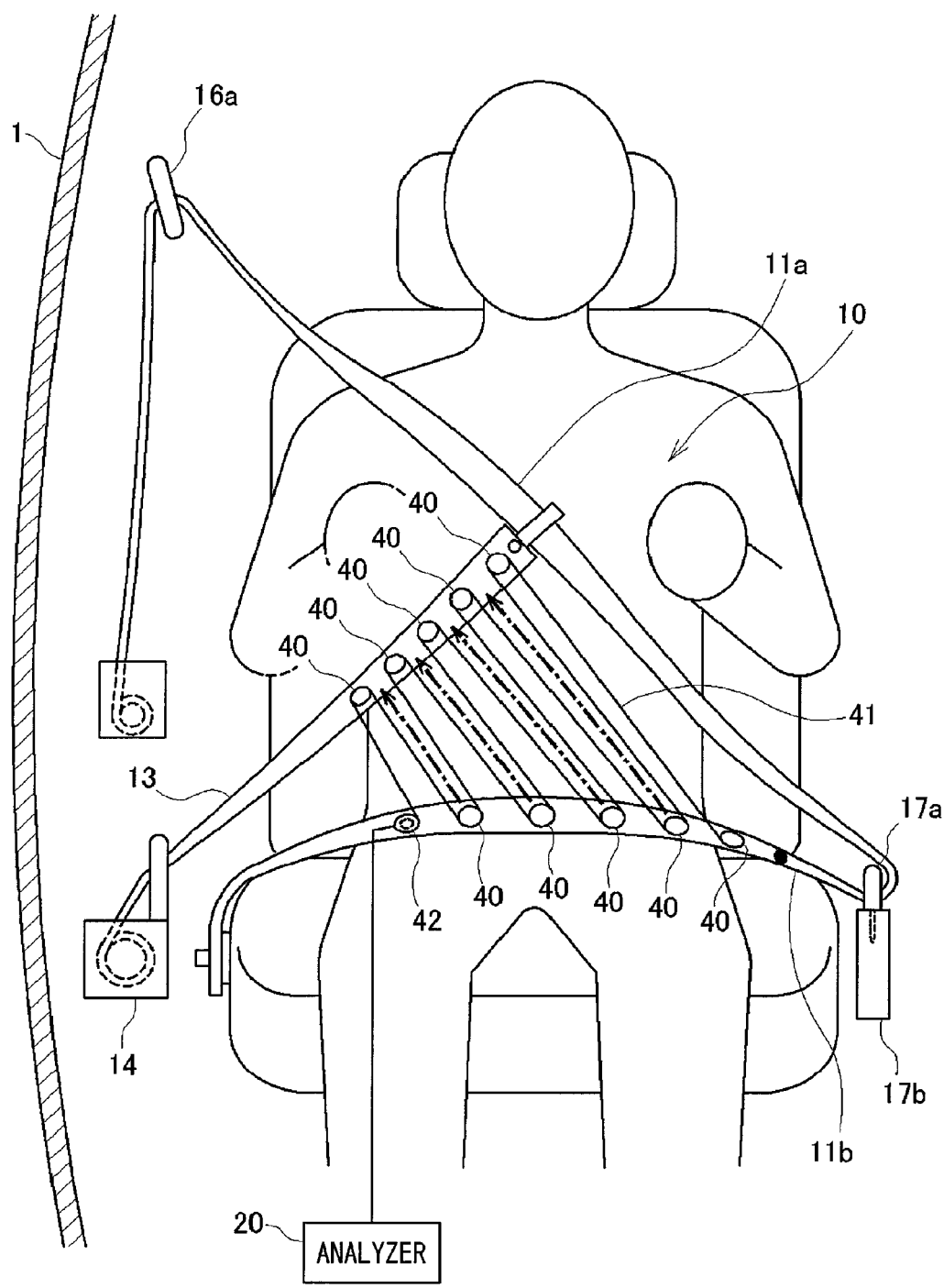
FIG. 6 is a view showing a respiratory detection device according to a modification in the equipped state, the respiratory detection device configured to detect a motion of an abdomen of an occupant between a sensor belt and a waist belt.

FIG. 6 shows a behavior of detecting a motion of an abdomen of an occupant between the sensor belt 13 and the waist belt 11b. As shown in the drawing, each of the sensor belt 13 and the waist belt 11b is equipped with multiple pulleys 40 at predetermined intervals. A tip end of a wire 41 is tied up with one of the pulleys 40 at the right end in the waist belt 11b in the drawing. An opposite end of the wire 41 is passed along one of the pulleys 40 at the right end of the sensor belt 13. Thereafter, the opposite end of the wire 41 is passed along the second of the pulleys 40 from the right end of the waist belt 11b. Subsequently, the wire 41 is passed around alternately between one of the pulleys 40 of the sensor belt 13 and one of the pulleys 40 of the waist belt 11b similarly to extend back and forth between the sensor belt 13 and the waist belt 11b from the right side to the left side in the drawing. Subsequently, the wire 41 is passed around one of the pulleys 40 at a left end of the sensor belt 13. Subsequently, the wire 41 is passed around a sensor 42, which is equipped to a left end of the waist belt 11b.

The sensor 42 has a function to apply a tensional force to wind up the wire 41. The tensional force causes the wire 41 to make contact with an abdomen of an occupant. In the present configuration, when an abdomen swells with occupants breathing, the wire 41 is pulled out. In addition, when the abdomen dents with occupant's breathing, the wire 41 is wound up. The sensor 42 rotates as the wire 41 is pulled out or as the wire 41 is wound up. The sensor 42 measures an amount of the wire 41 being pulled out (drawing amount) according to an amount of its rotation. The drawing amount of the wire 41 varies with a motion of an abdomen of an occupant. In consideration of this, similarly to above-described embodiment, the present configuration is enabled to detect a state of breathing of an occupant by connecting the analyzing device 20 to the sensor 42 and by analyzing a measurement result of the analyzing device 20.

In the present disclosure, the sensor 42 functions as a tensioning unit to apply a tensile force to the wire 41 to stretch the wire 41. It is noted that, the sensor 42 is not limited to the above-described sensor to measure the drawing amount of the wire 41. The sensor 42 may be a sensor configured to measure a variation in a tensional force of a wire.

The present configuration employs the wire 41 spread around the position of an abdomen of an occupant to measure the state of breathing of an occupant according to variation in the length of the wire 41. The present configuration measures a motion of an abdomen in a wide range. When an occupant's breathing is deep, an abdomen as a whole largely swells. In consideration of this, detection of a depth of breathing is enabled with more sufficient accuracy by measuring a motion of an abdomen in a wide range.

In addition, when an occupant turns the vehicular wheel largely and/or when an occupant (driver) views a diagonally backward of the vehicle 1, an upper portion of a body, in particular a body portion between a shoulder and a chest, is twisted. With the twisting of the upper portion of the body, the abdomen is also twisted slightly. Therefore, one of a right abdominal portion and a left abdominal portion protrudes forward, and the other of the right abdominal portion and the left abdominal portion retracts backward. In the present state, in a case where the detection range is local or pinpoint, a detection value tends to vary drastically to a negative side or a positive side. To the contrary, in the above-described case where the detection range is wide, the device measures both a negative factor and a positive factor of a measurement result. Consequently, the negative factor and the positive factor are offset to each other in the measurement result. Thus, a driving operation has less influential on the measurement result. Therefore, the present structure enables to detect the state of breathing, such as the length and the depth of breathing, with sufficient accuracy, even in a case where an occupant causes a movement such as twisting an upper portion of a body. In addition, the present configuration detects the state of breathing of an occupant according to the variation in the length of the wire 41. Therefore, the present configuration is less affected by an influence of an electromagnetic noise transmitted from the vehicle 1. In consideration of this, the present configuration enables to detect the state of breathing with sufficient accuracy.

As described above, even in the configuration where the wire 41 is spread around between the sensor belt 13 and the waist belt 11b, the respiratory detection device 10 according to the present modification is detachable and attachable similarly to the respiratory detection device 10 of the above-described embodiments. Specifically, when the seatbelt 11 is stored, the waist belt 11b and the sensor belt 13 are adjacent to each other in the stored state (refer to FIG. 2C and FIG. 5B). As sown by one-point chain arrows in FIG. 6, the positions of all the pulleys 40 are set, such that the pulleys 40 equipped to the sensor belt 13 and the pulleys 40 equipped to the waist belt 11b are alternately arranged. When being stored, the wire 41 is wound up by the sensor 42 to be shortened according to a distance between the sensor belt 13 and the waist belt 11b. Therefore, the wire 41 is stored while maintaining a state where the wire 41 is wound around the pulleys 40 equipped to the sensor belt 13 and is wound around the pulleys 40 equipped to the waist belt 11b alternately.

An occupant may perform a normal equipping operation of the seatbelt to change the respiratory detection device 10 in the stored state into the equipped state shown in FIG. 6. Specifically, when the occupant inserts the attachment-and-detachment plate 17a into the buckle 17b to equip the seatbelt 11, as described above with reference to FIG. 3, the sensor belt 13 is stretched and extended at a predetermined position. In the present state, as the distance between the sensor belt 13 and the waist belt 11b increases, the wire 41 is pulled out from the sensor 42. Therefore, without requiring a certain operation to an occupant, the wire 41 becomes to be in the equipped state where the wire 41 is spread around between the sensor belt 13 and the waist belt 11b.

It is noted that, it is also assumable that the wire 41 may be spread around between the shoulder belt 11a and the waist belt 11b, instead of being spread between the sensor belt 13 and the waist belt 11b. Herein, the shoulder belt 11a passes through the upper guide 16a and is to be located at the rear side when the seatbelt 11 is stored. Under the previous assumption, the wire 41 would be tangled between the shoulder belt 11a and the waist belt 11b when the seatbelt 11 is stored. Consequently, the state would be an obstacle for attachment and detachment of the seatbelt 11. To the contrary, as described above, the configuration of the present modification spreads the wire 41 around between the sensor belt 13 and the waist belt 11b, thereby to enable to windup the wire 41 without tangling when the seatbelt 11 is stored.

As above, the embodiments and modifications have been described. It is noted that, the present disclosure is not limited to the above embodiments and modifications and may be practiced in various forms.

For example, the present disclosure may be practiced by combining the embodiments and modifications. Specifically, for example, the waist belt 11b of the seatbelt 11 may be extended to form the extension belt 33, which may be equivalent to the sensor belt 13. In this case, the wire 41 may be spread around between the extension belt 33 and the waist belt 11b.

In addition or alternatively, operation information, such as information on a steering wheel and/or a brake pedal, may be acquired from the vehicle 1. In this case, a state of breathing may be detected without measurement result of the sensor 12 at the time of a driving operation. Even in this case, in which the measurement result at the time of a driving operation is excluded, the configuration produces the effect to enable to detect the state of breathing with sufficient accuracy by causing the sensor 12 to be in contact with an abdomen. Acceleration information on the vehicle 1 may be acquired from the vehicle 1. When the position of the vehicle 1 is inclined, it is conceivable that the position of an occupant is also inclined. On assumption that, similarly to the above description, the state of breathing may be detected without the measurement result of the sensor 12 when the position of the vehicle 1 is inclined.

Alternatively or for example, a sensor for measuring a motion of the seatbelt 11 may be equipped. In this case, a measurement result of the motion of the seatbelt 11 may be compared with a measurement result of the sensor 12. In this way, an influence caused by a driving operation and exerted on the measurement result of the sensor 12 may be compensated, and a state of breathing may be detected.

As described above, the respiratory detection device includes the detection belt and the sensor. The detection belt is connected to the seatbelt at the one-end side. The detection belt is mounted to the vehicle or the seat (driver's seat or occupant's seat) at the other-end side. The sensor detects behavior of breathing of an occupant. The detection belt retains the sensor at the position of an abdomen of the occupant. A behavior of breathing of an occupant appears further significantly on abdomen than a shoulder, a chest, or a waist. In addition, an abdomen is softer than a shoulder, a chest, and a waist. Therefore, a motion of a body caused by a driving operation hardly appears on an abdomen compared with a shoulder, a chest, and a waist. In consideration of this, the detection belt is caused to retain the sensor at the position of an abdomen of an occupant to cause the sensor to detect a state of breathing of an occupant. This configuration enables to reduce an influence caused by a driving operation and enables to detect the state of breathing of an occupant with sufficient accuracy. In addition, the present configuration enables an occupant to equip the detection belt by equipping the seatbelt thereby to retain the sensor at the position of an abdomen of the occupant. Therefore, the present configuration does not require an occupant an extra burden to equip the sensor.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A respiratory detection device configured to detect a behavior of breathing of an occupant on a seat of a vehicle, the respiratory detection device comprising:
a seatbelt configured to be equipped by the occupant to retain the occupant at the seat;
a detection belt mounted to the vehicle or the seat at one-end side, the detection belt connected to the seatbelt at an other-end side, the detection belt configured to be equipped by the occupant together with the seatbelt when the occupant equips the seatbelt; and
a sensor connected to the detection belt and configured to detect the behavior of breathing, wherein the detection belt is configured to retain the sensor at a position of an abdomen of the occupant when the occupant equips the seatbelt.

2. The respiratory detection device according to claim 1, wherein the seatbelt is a three-point seatbelt including a shoulder belt and a waist belt, the shoulder belt is configured to press a chest of the occupant, the waist belt is configured to press a waist of the occupant, and the detection belt is connected to the shoulder belt at the other-end side.

3. The respiratory detection device according to claim 1, wherein the detection belt is at least partially in contact with the abdomen of the occupant when the occupant equips the seatbelt, the sensor is located at a portion of the detection belt, and the portion of the detection belt makes contact with the abdomen of the occupant when the occupant equips the seatbelt.

4. The respiratory detection device according to claim 2, further comprising:

a wire affixed to the detection belt or the waist belt at one end, the wire installed to extend back and forth between the detection belt and the waist belt for a plurality of times; and a tensioning unit equipped to an other end of the wire, the tensioning unit configured to apply a tensional force onto the wire to stretch the wire between the detection belt and the waist belt, wherein the sensor is equipped to the tensioning unit and is configured to detect a drawing amount of the wire or a change in the tensional force of the wire caused by a motion of the abdomen of the occupant.

\* \* \* \* \*